United States Patent [19]
Bova et al.

[11] Patent Number: 5,025,376
[45] Date of Patent: Jun. 18, 1991

[54] RADIATION TELETHERAPY IMAGING SYSTEM HAVING PLURAL IONIZATION CHAMBERS

[75] Inventors: Frank J. Bova; Lawrence T. Fitzgerald; Walter Mauderli, all of Gainesville, Fla.

[73] Assignee: University of Florida, Gainesville, Fla.

[21] Appl. No.: 251,529

[22] Filed: Sep. 30, 1988

[51] Int. Cl.[5] .................... G01T 1/185; H01J 47/04
[52] U.S. Cl. ...................... 364/413.26; 364/413.15; 250/385.1
[58] Field of Search ................ 364/413.26, 413.15, 364/413.22; 378/22, 28, 29, 30, 31, 32, 33; 250/385.1

[56] References Cited

U.S. PATENT DOCUMENTS

| | | | |
|---|---|---|---|
| Re. 32,164 | 5/1986 | Kruger | 378/22 X |
| 3,922,547 | 11/1975 | Proudian et al. | 378/30 |
| 3,970,844 | 7/1976 | Fenn, Jr. et al. | 378/29 |
| 4,147,936 | 4/1979 | Eickel | 378/28 X |
| 4,640,729 | 2/1987 | Fujii et al. | 250/385.1 X |
| 4,691,108 | 9/1987 | Steele | 250/385.1 |
| 4,751,391 | 6/1988 | Eberhard | 250/385.1 |
| 4,810,893 | 3/1989 | Meertens | 250/385.1 |

FOREIGN PATENT DOCUMENTS 0196138 10/1986 European Pat. Off. .
244292 11/1987 European Pat. Off. .

OTHER PUBLICATIONS

Van Herk, Meertens, "A Matrix Ionization Chamber Imaging Device for On-Line Patent Step-Up Verification During Radiotherapy", *Radiotherapy and Oncology*, vol. II (1988) pp. 369-378.

*Primary Examiner*—Clark A. Jablon
*Assistant Examiner*—Steven Kibby
*Attorney, Agent, or Firm*—Kerkam, Stowell, Kondracki & Clarke

[57] ABSTRACT

An apparatus and method are provided for imaging an object undergoing high energy irradiation, such as a patient being treated by radiation teletherapy, the apparatus employing an array of ion chambers in a detector, the detector being rotatable with respect to the object, the image being obtained by acquiring projection data from each of the ion chambers at a sequence of predetermined orientations, the projection data for each location being reconstructed into an image by convolution filtering or other reconstruction technique, and subsequently employed in a back-projection of all projection data, which may then be displayed on a video monitor. The detector employs a liquid fluorocarbon as the ionizing medium in the plurality of ion chambers.

29 Claims, 2 Drawing Sheets

RADIATION TELETHERAPY IMAGING SYSTEM HAVING PLURAL IONIZATION CHAMBERS

BACKGROUND OF THE INVENTION

1. Field of the Invention.

The present invention relates to imaging systems for use in imaging anatomical structures undergoing high energy irradiation such as that used in radiation teletherapy.

2. Description of Related Art.

Various imaging systems have been developed and used in medical diagnostic procedures, ranging in sophistication from basic x-ray film techniques to computerized tomography (CT) scanning techniques. These diagnostic procedures employ a low level of energy in irradiating the human body in order to avoid the harmful side effects experienced with high doses of radiation. Imaging is relatively easy to accomplish in such low energy irradiation systems, as the detection portions of such systems are capable of producing sufficiently high contrasts between various objects in the path of the radiation beam.

Notwithstanding the advances in the field of low energy diagnostic imaging, a problem has long existed in developing imaging systems for use with high energy irradiation, such as that used in radiation therapy, to ensure proper treatment or provide improved methods of treatment of certain cancer patients. Energy levels used in radiation therapy are generally greater than 1 million electron volts (MeV), and may typically range from 4 to 25 MeV. Proper treatment requires that an optimum level of radiation be directed at a specific portion of the patient's body, while at the same time minimizing the exposure of all other parts of the body to the radiation. The irradiated area for which it is desired to obtain images is commonly referred to as a radition target or treatment target. The entire field being irradiated is generally referred to as a radiation or treatment portal.

Various methods, systems and techniques have been employed since the early days of radiation therapy in order to effectuate the minimization of the harmful side effects of the high energy irradiation of the body. One technique for minimizing the harmful effects employs small, tailored radiation fields or portals in what is sometimes referred to as "customizing" the treatment.

There are also systems known which attempt to improve the quality and consistency of the radiation treatment sessions by using what is sometimes referred to as a "record and verify" system. The "record and verify" systems conduct system checks to confirm that the teletherapy unit is initialized with a predetermined set of parameters, including predetermined tolerances. While such systems improve the reproduceability of the machine parameters in a series of treatments, they provide no imaging capability or control over the proper patient positioning and/or teletherapy beam alignment. These systems are quite expensive, at times costing from $80,000 to $100,000 to equip one accelerator used to generate radiation.

X-ray film systems have been used in portal imaging, but the resolution of the images obtained is generally poor due to the large size of the radiation source. Even more significant in high energy radiation imaging, the x-ray film has poor dynamic range. Such film systems further generally lack the capability to use computer enhancement processes and techniques to improve the contrast of the image. In the high energy radiation therapy applications, where there is a lack of differential radiation absorption between soft tissue and bone, the x-ray film systems have substantial performance drawbacks. The film systems are also labor intensive, requiring many steps to be performed manually in obtaining film images.

It is desirable in imaging radiation portals during radiation therapy sessions to obtain two types of images. A first "localization" image is obtained in order to ensure proper positioning of the patient within the portal or target area. Short bursts of radiation are employed prior to the actual treatment session and the position of the patient may be adjusted upon review of the "localization" image data. It is also desirable to obtain a second image, termed a "verification" image, which is a single image of the target area obtained for the entire treatment session, in order to provide a record image of that session.

The apparatus and method disclosed in U.S. Pat. No. 4,365,341, to Lam, employs a solid-state detector which is used to detect intermittent high-energy pulses in an attempt to ensure proper patient positioning during the treatment session. Solid-state detectors, such as those disclosed in Lam, possess at least two disadvantages when employed in a high-energy detection system of this type. Use of a matrix or linear array of detectors will generally not be feasible for use in imaging from a cost standpoint, even when using elements 2 mm in diameter (assuming circular detectors are employed) which yield a 4 mm spatial resolution. A 50 cm × 50 cm imaging array, for example, would require a matrix of 62,500 individual detectors. This number could be reduced by employing a linear array and translating the array as indicated in the Lam patent, however, a large number of detectors would still be required. Perhaps more importantly, a complete scan of the target area using such a device in order to obtain an image of the entire target would be very time consuming, rendering such a system impractical for clinical application. Additionally, solid state detectors are susceptible to radiation damage, and are therefore not practical for repeated use in detecting a high energy therapeutic beam. Damage from one week of exposure to such radiation, for example, could cause significant changes in the sensitivity of the solid-state detector elements.

Attempts have also been made at obtaining real time imaging during treatment using a fluorescent screen and video camera. Such systems produce images comparable to those obtained by x-ray film, and have the advantage over film that the image contrast may be enhanced by computer. The large size of such a fluorescent screen imaging device is a drawback in that its applications are limited to only certain angles when used in conjunction with a teletherapy machine.

Ion chambers of widely differing designs have heretofore been used for detecting radiation in various systems. Ion chambers previously disclosed as being used in connection with high-energy x-ray therapy equipment have generally been limited to detection of incident radiation in order to assist in aligning the beam of radiation. As seen in U.S. Pat. No. 3,955,089, to McIntyre et al, an x-ray therapy application, the ion chambers are used merely to detect the presence of radiation, and are used to surround the incident beam of radiation in order to assist in steering the beam into proper alignment. The ion chambers in this patent are not used to provide an imaging capability, as they are disposed on the incident beam side of the patient undergoing treatment. Overall, prior devices and methods have not provided those practicing in the radiation oncology field, and more particularly those directly involved in conducting radiation therapy, with good quality, low cost imaging of the radiation portal without also providing significant disadvantages associated with the systems.

It is therefore an important object of the present invention to provide an apparatus for obtaining images and visualizing the treatment portal during radiation therapy sessions.

It is a further important object of the present invention to provide an apparatus for obtaining images of the treatment portal which employs a detector comprising a plurality of ion chambers in a parallel array in combination with means for rotating the strip detector to collect image data over the area of the treatment portal.

It is a further important object of the present invention to provide an apparatus for obtaining images of the treatment portal which employs an accurate stepping motor as the means for rotating the detector, and further providing means for measuring small ionization currents generated in the array of ion chambers.

It is a further object of the present invention to provide ion chambers having parallel opposed electrodes and containing an ionizing medium of a liquid fluorocarbon material.

It is another important object of the present invention to provide a method for imaging the treatment portal and target during radiation therapy for obtaining localization and verification images which comprises the steps of generating a high energy radiation beam, directing the beam toward an area of the body to be treated, thereby creating a radiation portal, obtaining readings of absorbed radiation from the radiation target area using an array of ion chambers as a detector, measuring the ionization current at each ion chamber using a repetitive integral measurement technique, and reconstructing an image from the individual measurements by employing a convolution filtered back-projection technique or other reconstructive technique.

SUMMARY OF THE INVENTION

The above and other objects of the present invention are accomplished by providing an apparatus having a detector adapted to be used in connection with a radiation teletherapy machine. The detector, which comprises an array of ion chambers aligned in a parallel, side-by-side manner, is positioned on the side of the patient being treated opposite that of the beam of radiation generated by the teletherapy machine. The detector is thus capable of detecting the radiation transmitted through the patient, and is designed to be capable of detecting varying levels of transmitted radiation.

A stepping motor and associated hardware are provided to permit movement of the detector in a rotational mode in order to detect the transmitted radiation at various orientations, in order to reconstruct images of the treatment portal area. The stepping motor is interfaced with and controlled by a microcomputer which also receives imaging information from an amplifier network provided for processing the signals from the detector.

Each of the ion chambers of the present invention employed in the detector comprises a pair of parallel electrodes having a liquid ionizing medium disposed between the electrodes. The use of a liquid ionizing medium yields a high level of radiation absorption, which thereby increases the signal strength.

The image-obtaining method or process employing the detector in the present invention begins with moving the patient into position wherein the appropriate part of the body, e.g., a tumor-bearing portion of the body, is disposed to be in the path of a beam of radiation once the teletherapy machine is activated to produce the beam. The detector is positioned to be exposed to radiation transmitted through the patient's body in the treatment portal. The treatment is commenced by activation of the beam, and the radiation transmitted through the patient is detected by the array of ion chambers functioning as a detector.

The detector will remain in its initial position for a predetermined period of time, and an ionization current will be produced in, and measured from, each ion chamber, the ionization currents being proportional to the amount of radiation absorbed by the ionizing medium disposed between each pair of electrodes forming the ion chambers.

An amplifier network is used to measure the ionization current by integration, the measured current then being converted to digital information capable of being used to produce an image. The detector may be moved through a precise incremental rotation pattern by the stepping motor with the ionization current of each chamber being measured at each increment, thus permitting projection data to be acquired from a plurality of orientations. Alternatively, the detector may be continuously rotated through a pattern with measurements being taken while the detector is in motion. The technique employed in reconstructing images by collection of projection data with such a detector, which is considered to be a series of apertures, is sometimes referred to as coded aperture imaging.

The information collected from each ion chamber is filtered, and the filtered information from the individual ion chambers is assembled together or "added", and subsequently back-projected to produce an image of the entire detection area, for example, the area of the treatment portal.

BRIEF DESCRIPTION OF THE DRAWINGS

These and other features of the present invention and the attendant advantages will be readily apparent to those having ordinary skill in the art and the invention will be more easily understood from the following detailed description of the preferred embodiment of the present invention taken in conjunction with the accompanying drawings wherein like reference characters represent like parts throughout the several views, and wherein.

DETAILED DESCRIPTION OF THE PREFERRED EMBODIMENT

Figure 1:
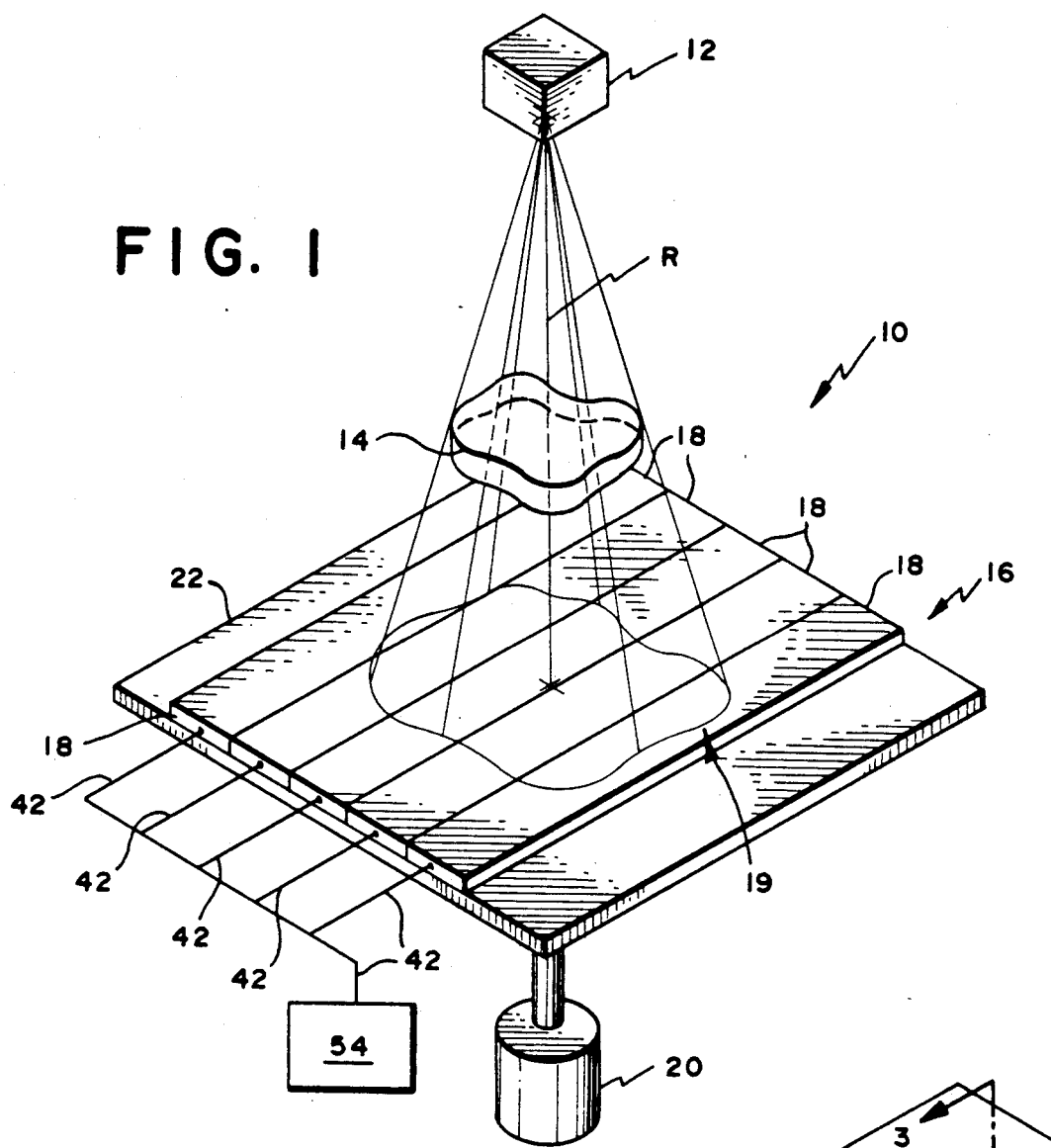
FIG. 1 is a perspective view of the radiation teletherapy imaging system of the present invention, with several of the components being depicted in schematic form.

Referring initially to FIG. 1, the radiation teletherapy imaging system and apparatus according to a preferred embodiment of the present invention is referred to generally by numeral 10. The radiation source 12, shown schematically, will be housed in a teletherapy machine (not shown) such as the schematically depicted machine in U.S. Pat. No. 4,365,341, to Lam. Object or mass 14 is representative of the object being irradiated, such as the body of a patient in the instance of a radiation therapy application. As can readily be seen, the imaging system 10 is disposed at the side of mass 14 opposite that of radiation source 12, thereby being exposed to the radiation transmitted through the object.

Figure 2:
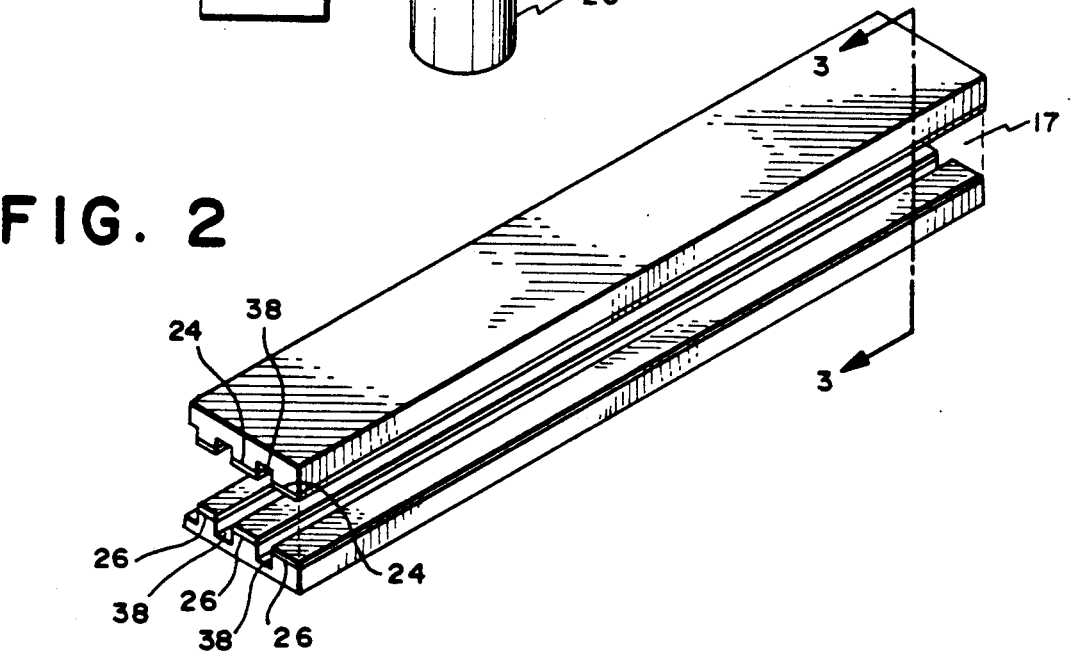
FIG. 2 is a perspective view depicting the positioning of the parallel electrodes relative to one another in the detector of the present invention.

The imaging system 10 employs a detector 16, comprising a plurality of longitudinally extending ion chambers 18, the construction of which will be discussed in more detail later. The detector 16 preferably has a length or longitudinal extent sufficient to span a maximum portal or target dimension, and a total width of ion chambers sufficient to span a maximum portal or target dimension transverse to the longitudinal extent. For example, the detector may be on the order of 40 cm by 40 cm, or 50 cm by 50 cm, for use with a typical radiation portal or target area 19. The detector comprising the array of ion chambers 18 is sealed and filled with an ionizing medium, and the space occupied by this ionizing medium may be referred to as a sensitive volume 17 (FIG. 2).

In the preferred embodiment of the present invention, means for rotating the detector 16 about vertical axis R within the portal imaging area is provided in the form of stepping motor 20. The stepping motor 20, shown in schematic form, can be selected from commercially available units suitable for use with the present system.

Stepping motor 20 is adapted to effect precise incremental rotation of the detector 16, and it may be desired, in certain instances, to provide a motor having a capability for accurately and continuously rotating the detector 16. Rotational stepping motor 20 is preferably coupled to the underside of a table 22 and is disposed to rotate table 22 about a vertical (as shown) rotational axis R running through the center of the table. The table 22 itself is generally to be of a size approximating but slightly larger than the periphery of the maximum treatment portal to be imaged in a particular teletherapy machine, and is to have sufficient strength to support detector 16. The rotational axis R is also preferably colinear with a centerline of the radiation beam emanating from radiation source 12.

The construction of detector 16 is best described with reference to FIGS. 2 and 3. Detector 16 has a plurality or an array of front surface electrodes 24, each electrode having a longitudinal extent, the electrodes 24 being disposed in a parallel, side-by-side manner, the electrodes further being spaced apart from each other at a predetermined distance. An associated plurality or array of back surface electrodes or collecting electrodes 26 are disposed to be facing the front surface electrodes 24. In the preferred embodiment, each of the plurality of collecting electrodes 26 is of the same size as, and is disposed parallel to and in alignment with, an associated front surface electrode 24. As used herein, the term "front" refers to a side of detector 16 which is nearest the radiation beam or source 12, and the terms "back" and "rear" refer to the side of the detector farthest from the beam.

Figure 3:
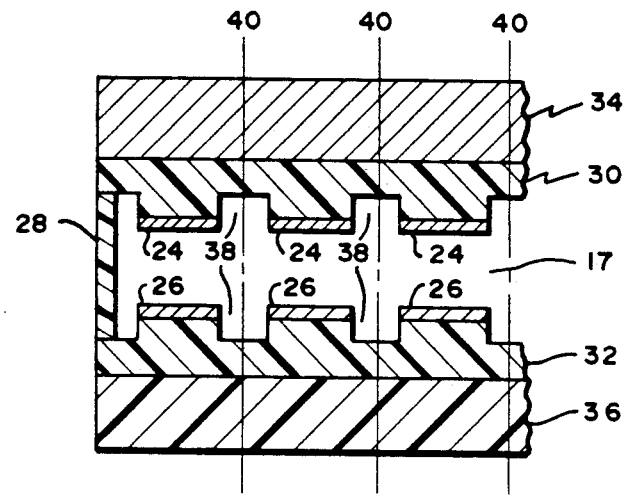
FIG. 3 is a cross-section of a portion of the upper and lower electrodes comprising the array of ion chambers, taken along section line 3—3 of FIG. 2.
Figure 3A:
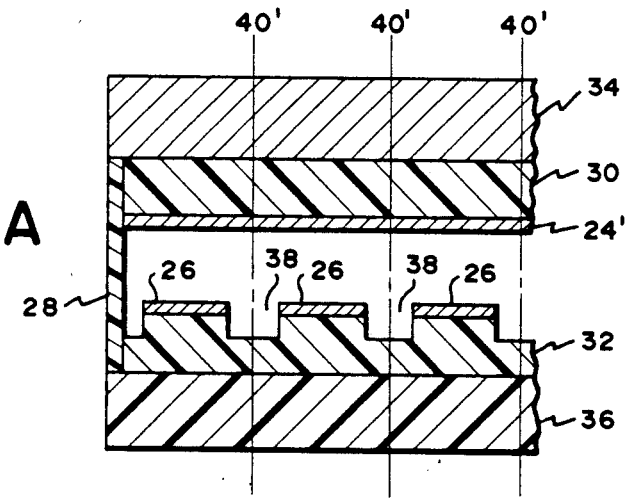
FIG. 3a is a cross-section of an alternate embodiment of the detector shown in FIG. 3.

An alternate construction of detector 16 is depicted in FIG. 3a. In this embodiment, detector 16 has a continuous front surface electrode 24' the conducting surface of which extends across the entire width and longitudinal extent of detector 16. The array of collecting electrodes 26 facing the front surface electrodes in this embodiment is identical to the array of collecting electrodes depicted in FIG. 3.

The front surface and collecting electrodes 24, 26 are spaced apart at a predetermined distance. The spacing between the two arrays of electrodes 24, 26 is preferably maintained by side wall members 28 (FIG. 3) which are bonded to the front and back surface electrodes around the entire peripheral edge of the electrodes. In a preferred embodiment of detector 16, the vertical spacing between the array of front surface electrodes 24 and the array of collecting electrodes 26 may be on the order of 2 mm.

Side wall members 28 are preferably accurately machined spacer elements made of a styrene copolymer or other polymeric compound which possesses good dielectric properties and whose properties are not significantly affected by exposure to radiation. An example of a polymer suitable for use is the styrene copolymer Rexolite®(registered trademark of American Enka Corporation). Side walls 28 are bonded to front and back surface electrodes 24, 26 in a liquid-tight manner about the entire periphery of the electrodes, thus forming the totally enclosed sensitive volume 17 of the detector 16, which is used to contain the ionizing medium. One of side wall members 28 will preferably have a fill hole (not shown) for introducing the ionizing medium into the sensitive volume.

In a preferred embodiment, the front surface electrodes 24, 24' and the plurality of collecting electrodes 26 may each be made from a copper-plated circuit board 30, 32 with the conductive surfaces of the electrodes comprising a thin copper foil. The circuit boards 30, 32 may be bonded to front and back surface backing plates 34, 36, which preferably structurally reinforce the circuit boards 30, 32. The front surface plate 34 functions to provide additional material thickness through which the incident radiation must pass before entering the ionizing medium. This additional thickness produces an electronic buildup on the front surface electrode 24 as the beam of radiation passes through the front surface support plate before entering the sensitive volume 17 of detector 16 containing the ionizing medium. The additional thickness is generally required to reduce the number of scattered electrons and low energy photons reaching the sensitive volume 17 of the detector 16 in relation to the number of primary electrons, or stated another way, to increase the ratio of primary electrons to scattered radiation. This will permit the ion chambers 18 to attain an electronic equilibrium, thereby enabling the chambers to produce readable measurements.

Suitable materials for construction of the front surface plate 34 include metals such as tungsten, copper, and lead. Preferences in selecting the particular material for front surface plate 34 will be higher density materials (to reduce required thickness) and low cost. Back surface backing plate 36 may preferably be made of an acrylic plate material, which will primarily provide structural support, but also will preferably reduce the amount of backscattered electrons in the detector 16.

FIG. 3 depicts the arrangement and alignment of the front surface electrodes 24 and the associated collecting electrodes 26 in detector 16. Each of the front surface electrodes 24 is spaced apart from its adjacent front surface electrodes by longitudinal channels 38. The collecting electrodes 26 are spaced apart in a like manner, and the collecting electrodes are aligned underneath corresponding or associated front surface electrodes. In the embodiment wherein these electrodes are constructed from circuit boards, these longitudinal channels 38 would comprise the gaps between the conductive foil surfaces where the backing board is exposed. The channels 38 may be created by etching away portions of the copper layer, which would leave exposed a phenolic backing board. Although the channels 38 provide the only physical separation between the adjacent electrodes, i.e. no vertical walls extend between adjacent pairs of electrodes, the spacing between the adjacent pairs of electrodes permits the pairs to function as individually measurable ionization currents. Broken lines 40 in FIG. 3 are used to depict, in this cross-sectional view, the individual ion chambers 18 formed by associated pairs of front surface electrodes 24 and collecting electrodes 26.

In the FIG. 3a embodiment, it can be seen that use of a continuous conductive surface for front surface electrodes 24' avoids the necessity to provide channels between the electrodes. This design also avoids the additional manufacturing task of having to align each of the collecting electrodes 26 with a specific front surface electrode. Both of these features of this embodiment have the potential to reduce manufacturing costs while sacrificing little, if any, performance. The channels 38 between the collecting electrodes in this embodiment permits the detector 16 to function as an array of individually measurable ion chambers. Broken lines 40' are used to depict the individual ion chambers 18 in this view.

It should be noted, that, in the partially schematic view of FIG. 1, the array of ion chambers 18 shown is preferably constructed in accordance with the embodiment shown in FIG. 2 and 3, and 3a the lines in FIG. 1 separating the individual ion chambers 18 being intended to represent functional separations rather than physical dividers.

In operation, an electric field is produced between the associated pairs of front surface and collecting electrodes 24, 26 by applying an electric potential across the electrodes. In the embodiments described above, wherein no vertical walls separate the adjacent ion chambers 18 from one another, the spacing between the adjacent chambers must be at least wide enough to ensure that the electromagnetic lines of force created between one associated pair of front surface electrodes and collecting electrodes 24, 26 do not interfere with the electric fields established between adjacent associated pairs of front surface and collecting electrodes. Where the electrodes employed have a width on the order of 2 mm, this inter-chamber spacing may be on the order of 0.15 mm. It is to be noted that the spacing of the collecting electrodes 24 in the FIG. 3a embodiment would preferably be on the same order. Using these dimensions, a detector 16 designed to image an area 50 cm in width would require on the order of two hundred and fifty (250) associated pairs of electrodes functioning as individual ion chambers 18. The use of individual electrodes having a width of 2 mm will yield a spatial resolution of 4 mm.

The imaging is performed in this preferred embodiment using quantitative measurements taken from each of the collecting electrodes 26 in the array of ion chambers. The measurement will be of an ionization current generated in each ion chamber 18 by the absorption of radiation reaching detector 16.

The ionizing medium employed in the detector 16 according to a preferred embodiment of the present invention is a liquid fluorocarbon, marketed under the trademark FLUORINERT FC-104 by the 3M Company (Minnesota Mining and Manufacturing), although the use of other ionizing media, primarily in liquid form, is envisioned. The ionizing medium fills the volume between electrodes 24, 26, termed the sensitive volume 17. FLUORINERT FC-104 was selected in the present invention due to its potential for yielding higher signal strengths in the array of ion chambers 18, and also because of its inertness (non-flammability). Further desirable characteristics of FLUORINERT FC-104 for use in this service include the capability of using the medium a substantially room temperature, and that the FLUORINERT does not act as a solvent with respect to the materials of construction of detector 16. Other liquid fluorocarbons marketed under the FLUORINERT name would also be suitable for use. A possible alternative ionizing medium is liquid iso-octane (2-2-4-trimethyl pentane) which also would yield high signal strengths, but has the disadvantage of being flammable.

The response characteristics of liquid ionizing media, e.g. rise and decay times, must be suitable for use in an ion chamber to be used in teletherapy imaging. Liquids in general have a lower charge mobility or ion mobility than gases, more time therefore being required to collect the charges liberated in radiation absorption. Uncollected charges resulting primarily from slow response characteristics will produce afterglow effects where the charges are not collected prior to the initiation of a subsequent measurement. The above-mentioned liquids have been determined through experimentation to have suitable rise and decay characteristics for use in the radiation therapy imaging service.

The method and process for acquiring the data to be used in producing images of radiation portals with the apparatus of the present invention will now be described in further detail. Quantitative measurements are taken, according to a preferred method of the present invention, from each ion chamber 18 of the array for a predetermined time period, the measurements later being processed to form a complete image. Lines 42 (FIG. 1) are shown as a schematic representation of the circuit lines used to measure the ionization current at the collecting electrodes 26 in the individual ion chambers 18 in the array. The image reconstruction performed in accordance with the present invention involves collecting what is referred to as projection data, whereby an image of, for example, a two-dimensional distribution, is determined from estimates of line integrals along a finite number of lines of known location.

Figure 4:
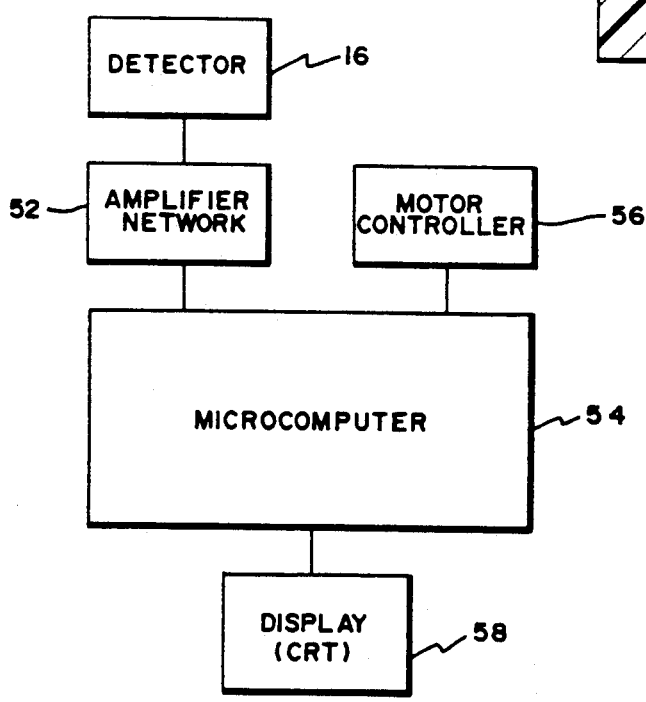
FIG. 4 is a block diagram showing the interaction of the components of the imaging apparatus of the present invention.

An amplifier network 52, shown in the block diagram of FIG. 4 is employed to measure the ionization current generated by each ion chamber 18 of detector 16 to produce projection data associated with the radiation absorbed by the ionization medium in each chamber at its particular location. Very small ionization currents, on the order of a picoampere, are required to be measured in this system with high accuracy. Before a first measurement is commenced, an electrometer system which forms a part of the amplifier network 52 is initialized to zero (0) volts. The orientation of detector 16, which may be moved through a series of rotations during the imaging process, may be initialized prior to commencement of measurements at what may be considered a 0° orientation.

A microcomputer, shown at block 54 of FIG. 4 is interfaced with the components and assists in controlling the components during the imaging process. Microcomputer 54 may preferably be programmed with a predetermined time interval during which a measurement will be made of the individual ionization currents in the array of ion chambers 18 at each orientation of detector 16. When radiation source 12 begins to irradiate object 14, microcomputer 54 commences a timing of a first of the predetermined time intervals. During this time, detector 16 remains stationary, and amplifier network 52 measures the ionization current generated by the radiation absorption of the ionizing medium at each of the collecting electrodes 26 in the array of ion chambers 18.

The ionization currents are integrated, or in other words are measured by the amplifier 52 using a repetitive integral measurement technique. The current integration is conducted and is stopped at the end of the predetermined time period, and an analog-to-digital conversion is performed to convert the integrated signal into digital form to obtain projection data associated with each position or location of the plurality of ion chambers 18. As noted previously, in certain instances it will be desirable to conduct the imaging process by rotating the detector 16 through a plurality of imaging angles. Imaging in such situations is generally accomplished in a series of discrete measurements performed for predetermined time periods. When the end of a predetermined measurement interval is reached, microcomputer 54 sends a signal through an interface to a motor controller 56, which in turn sends pulses to the stepping motor 20, resulting in a movement of detector 16 to a second predetermined measurement orientation.

Before beginning a new measurement at this new orientation, the electrometer system in the amplifier network is reset to the initialized, zero voltage setting. The process for measuring the ionization currents described above is repeated to measure the magnitude of radiation detected and absorbed by the ionizing medium of the ion chambers 18 at the new orientation, and all subsequent orientations thereafter.

The microcomputer 54 and motor controller 56 are preferably programmed to conduct a predetermined sequence of rotation of detector 16 in order to obtain data from a desired area, for example, the area circumscribed by the radiation target area in a radiation teletherapy machine. For obtaining a verification image of an entire treatment session projection data will preferably be obtained for multiple views between zero and 180 degrees through this sequence of rotation of detector 16. Localization images will generally not include data from multiple orientations, as these images are obtained from short bursts of the radiation beam prior to a treatment session.

The microcomputer 54 also preferably possesses the capability to perform a convolution filtering of the projection data obtained at each individual ion chamber 18 and at each detector position. Convolution filtering in general is a technique for mathematically filtering data, and the convolution filtering of data acquired in the imaging apparatus of the present invention may be performed by methods and using algorithms generally known in the art. A particular advantage in using an array of ion chambers 18 as the detector in combination with the convolution filtering of data obtained at the plural discrete locations is that while the detector is making a measurement at a new measurement orientation, or merely taking a new or different measurement at the same orientation, microcomputer 54 is capable of filtering the previously obtained data at the same time the new measurement is being made. Thus, much processing time can be saved in obtaining a final image to be displayed. Additionally, obtaining projection data from the entire target area at every measurement interval through the use of the array of ion chambers eliminates other factors contributing to delay in displaying a final image. For example, there is no need to perform a scan of the target area to collect measurements across the entire target area before being able to display the image. This is especially advantageous where localization images are being obtained.

Once the detection and measurement of the absorbed radiation in the area of interest are complete, in accordance with the predetermined sequence of rotation (where such a sequence is being employed), and after the individual projections are filtered, microcomputer 54 will preferably be designed and programmed to perform an "addition" of the filtered projection data. Such a process is termed a "back-projection" in the art. In the preferred embodiment, which employs a convolution filtering of the individual projections prior to the back-projection, the entire image reconstruction process is referred to as a convolution filtered back-projection method. This method has the advantage in the high-energy radiation imaging process of permitting production and display of images at five or ten second intervals and even more frequently. Performing the convolution filtering prior to back-projection further produces a much better image by vastly reducing background noise tending to reduce the image-to-background contrast.

It is envisioned that the detector 16 of the present invention will be suitable for use with other reconstructive techniques which may provide increased image processing speed, as well as the capability to obtain projection data while the detector is moving in rotation, which would avoid the requirement to freeze the detector 16 at specific increments.

In the preferred embodiments of the present invention, the image is displayed after reconstruction on a video display tube or cathode ray tube 58 through the use of a video frame grabber conventionally employed in data acquisition and display systems. The apparatus and method of the present invention are capable of producing and displaying images of a quality not heretofore believed attainable in the imaging of anatomical structures in a high-energy megavoltage radiation portal or target area.

Although specific details and elements have been specified in the foregoing description of the preferred embodiment, it is to be appreciated that these are for illustrative purposes only. Numerous modifications and adaptations may readily become apparent to those skilled in the art. Accordingly, the scope of the present invention is to be determined by reference to the appended claims.

What is claimed is:

1. Apparatus for imaging a high energy beam of radiation emanated from a radiation source and transmitted through an object comprising:
   detector means for quantitatively measuring and detecting said transmitted radiation, said detector means comprising a plurality of ion chambers each of said ion chambers having a longitudinal extent, said ion chambers being disposed in a parallel, side-by-side manner whereby said detector means comprises a parallel array of said longitudinally extending ion chambers;
   said plurality of ion chambers comprising at least a first front surface electrode and a plurality of substantially parallel, longitudinally extending collecting electrodes disposed to be facing said front surface electrode and spaced apart at a predetermined distance, wherein said plurality of ion chambers has a predetermined total width at least as great as a maximum width dimension of a target area to be imaged, and wherein said longitudinal extent of each of said plurality of ion chambers has a predetermined length at least as great as a maximum length dimension of said target area,
   said detector means being disposed on a side of said object opposite that of said radiation source;
   means for converting an ionization current measured by each of said ion chambers into projection data representative of an amount of radiation absorbed by each of said ion chambers;
   means for converting said projection data obtained from each of said ion chambers into a single projection containing data measured from each of said ion chambers; and
   means for displaying said single projection.

2. Apparatus as defined in claim 1 wherein said plurality of ion chambers comprises a plurality of front surface electrodes and an associated plurality of collecting electrodes.

3. Apparatus as defined in claim 2 wherein said front surface electrodes are disposed on a first backing member, and said associated collecting electrodes are disposed on a second backing member, said front surface electrodes being aligned in a side-by-side manner and further being spaced apart from adjacent front surface electrodes at a predetermined distance, said associated collecting electrodes being aligned in a side-by-side manner and further being spaced apart from adjacent collecting electrodes at a predetermined distance substantially identical to said spacing between adjacent front surface electrodes.

4. Apparatus as defined in claim 3 wherein said first backing member and said second backing member are maintained in a spaced apart relation by a sidewall extending between said backing members around an entire peripheral edge of said backing members, said sidewall having a predetermined height sufficient to produce said predetermined spacing between said front surface electrodes and said collecting electrodes, said sidewall and said first and second backing members further defining a volume in said detector means in which an ionizing medium is to be disposed.

5. Apparatus as defined in claim 1 wherein an ionizing medium disposed between said front surface electrode and said collecting electrodes comprises a liquid.

6. Apparatus as defined in claim 1 wherein a first backing member and said front surface electrode disposed thereon comprise a first circuit board, and wherein a second backing member and said collecting electrodes disposed thereon comprise a second circuit board, said first and second circuit boards having a non-conductive backing layer and facing surface of conductive material said second circuit board having a plurality of substantially parallel, longitudinally extending strips of a conductive material spaced apart at a predetermined distance.

7. Apparatus for imaging a high energy beam of radiation emanated from a radiation source and transmitted through an object comprising:
   detector means for quantitatively measuring and detecting said transmitted radiation, said detector means comprising a plurality of ion chambers, each of said ion chambers having a longitudinal extent, said ion chambers being disposed in a parallel, side-by-side manner whereby said detector means comprises an array of said ion chambers;
   said plurality of ion chambers comprising at least a first front surface electrode and a plurality of substantially parallel, longitudinally extending collecting electrodes disposed to be facing said front surface electrode and spaced apart at a predetermined distance, wherein said plurality of ion chambers has a predetermined total width at least as great as a maximum width dimension of a target area to be imaged, and wherein said longitudinal extent of said plurality of ion chambers has a predetermined length at least as great as a maximum length dimension of said target area,
   said detector means being disposed on a side of said object opposite that of said radiation source;
   means for converting an ionization current measured by each of said ion chambers into projection data representative of an amount of radiation adsorbed by each of said ion chambers;
   means for converting said projection data obtained from each of said ion chambers into a single projection containing data measured from each of said ion chambers;
   means for displaying said single projection;
   wherein an ionizing medium disposed between said front surface electrode and said collecting electrodes comprises a liquid; and
   wherein said liquid ionizing medium comprises a non-flammable liquid fluorocarbon.

8. Apparatus for imaging a high energy beam of radiation emanated from a radiation source and transmitted through an object comprising:
   detector means for quantitatively measuring and detecting said transmitted radiation, said detector means comprising a plurality of ion chambers, each of said ion chambers having a longitudinal extent, said ion chambers being disposed in a parallel, side-by-side manner whereby said detector means comprises an array of said ion chambers;
   said plurality of ion chambers comprising at least a first front surface electrode and a plurality of substantially parallel, longitudinally extending collecting electrodes disposed to be facing said front surface electrode and spaced apart at a predetermined distance, wherein said plurality of ion chambers has a predetermined total width at least as great as a maximum width dimension of a target area to be imaged, and wherein said longitudinal extent of said plurality of ion chambers has a predetermined length at least as great as a maximum length dimension of said target area, said detector means being disposed on a side of said object opposite that of said radiation source;

means for converting an ionization current measured by each of said ion chambers into projection data representative of an amount of radiation adsorbed by each of said ion chambers;

means for converting said projection data obtained from each of said ion chambers into a single projection containing data measured from each of said ion chambers;

means for displaying said single projection;

wherein a first backing member and said front surface electrode disposed thereon comprise a first circuit board, and wherein a second backing member and said collecting electrodes disposed thereon comprises a second circuit board, said first and second circuit boards having a non-conductive backing layer and facing surface of conductive material, said second circuit board having a plurality of substantially parallel, longitudinally extending strips of a conductive material spaced apart at a predetermined distance; and said apparatus further comprising means for increasing a ratio of primary electrons to scattered radiation to be detected by an ionizing medium of said detector means, said ratio increasing means being disposed adjacent to said first backing member on a side of said backing member opposite said front surface electrode, said ratio increasing means having length and width dimensions substantially equal to those of said first backing member, said ratio increasing means further having a predetermined thickness sufficient to adsorb at least a portion of the scattered radiation generated by said high energy beam of radiation when said beam is transmitted through said object.

9. Apparatus as defined in claim 8 wherein said ratio increasing means comprises a sheet of metallic material.

10. Apparatus as defined in claim 9 wherein said sheet is made of tungsten.

11. Apparatus as defined in claim 9 wherein said sheet is made of copper.

12. Apparatus for imaging a high energy beam of radiation emanated from a radiation source and transmitted through an object comprising:

detector means for quantitatively measuring and detecting said transmitted radiation, said detector means comprising a plurality of ion chambers, each of said ion chambers having a longitudinal extent, said ion chambers being disposed in a parallel, side-by-side manner whereby said detector means comprises an array of said ion chambers;

said plurality of ion chambers comprising at least a first front surface electrode and a plurality of substantially parallel, longitudinally extending collecting electrodes disposed to be facing said front surface electrode and spaced apart at a predetermined distance, wherein said plurality of ion chambers has a predetermined total width at least as great as a maximum width dimension of a target area to be imaged, and wherein said longitudinal extent of said plurality of ion chambers has a predetermined length at least as great as a maximum length dimension of said target area, said detector means being disposed on a side of said object opposite that of said radiation source;

means for converting an ionization current measured by each of said ion chambers into projection data representative of an amount of radiation adsorbed by each of said ion chambers;

means for converting said projection data obtained from each of said ion chambers into a single projection containing data measured from each of said ion chambers;

means for displaying said single projection; and said apparatus further comprises means for rotating said detector means.

13. Apparatus as defined in claim 12 wherein said rotating means is adapted to be rotated in precise, discrete increments about a vertical axis with respect to said object; and means for controlling said rotating means, whereby said detector means is adapted to be moved through a predetermined sequence of orientations and whereby projection data may be obtained at each orientation of said sequence.

14. Apparatus as defined in claim 13 wherein said detector means is mounted on a table and said rotating means comprises a stepping motor adapted to rotate said table.

15. Apparatus as defined in claim 14 wherein said stepping motor is disposed to rotate said detector means about a rotational axis which is colinear with a center line of said beam of radiation.

16. Apparatus for imaging a high energy teletherapy beam of radiation transmitted through an object comprising:

a detector having a first plurality of front surface electrodes, each of said electrodes having a longitudinal extent, a second plurality of collecting electrodes, each of said collecting electrodes having a longitudinal extent, wherein each of said front surface electrodes has a collecting electrode associated therewith, each pair of associated front surface and collecting electrodes extending in a parallel, spaced apart manner, the pairs of associated electrodes thereby forming a plurality of ion chambers adapted to measure a quantity of radiation absorbed by an ionizing medium disposed between each pair of associated front surface and collecting electrodes;

means for converting said measurement of said radiation absorbed by each of said plurality of ion chambers of said detector into digital projection data representative of an amount of radiation absorbed by each of said plurality of ion chambers;

means for rotating said detector about a vertical axis with respect to said teletherpy beam and said object;

means for controlling said rotating means to rotate said detector through a predetermined sequence of orientations;

means for converting projection data obtained at each orientation of said detector into a single projection containing data from all of said orientations; and means for displaying said projection data.

17. Apparatus as defined in claim 16 wherein said detector is mounted on a table and said rotating means comprises a first stepping motor adapted to rotate said table.

18. Apparatus as defined in claim 17 wherein said rotating means comprising said first stepping motor is disposed to rotate said table about a rotational axis which is colinear with a centerline of said beam of radiation.

19. Apparatus as defined in claim 16 wherein each of said electrodes has a conductive surface made of a copper foil.

20. Apparatus as defined in claim 16 wherein said detector further comprises an amplifier network adapted to measure an ionization current produced in each of said ion chambers by current integration.

21. Apparatus as defined in claim 20 wherein said means for converting said projection data into said single projection comprises a computer, said computer being adapted to individually filter said projection data obtained at each position of said strip detector by a convolution filtering process prior to converting said data into said single projection.

22. Apparatus for measuring and displaying an image of high energy, megavoltage radiation transmitted from a radiation source through an object, such as a patient undergoing radiation therapy, comprising:

a detector comprising a plurality of ion chambers, each of said ion chambers having a longitudinal extent, each of said ion chambers further having a front surface electrode and a collecting electrode, and having an ionizing medium disposed between said electrodes, each of said plurality of ion chambers being disposed immediately adjacent to at least one other of said plurality of ion chambers, said plurality of ion chambers forming a detector array disposed perpendicularly to a centerline of a radiation beam emanating from said radiation source;

a motor adapted to rotate said detector with respect to said object;

means for controlling said motor, whereby said detector may be moved through a predetermined sequence of orientations for obtaining ionization current measurements from each of said ion chambers at each orientation of said sequence;

measuring means for integrating said ionization current produced in each of said ion chambers at each orientation;

means for converting said ionization current measurements into digital form;

means for performing a convolution filtering of said measurements in digital form;

means for back-projecting all of said measurements into a single projection; and means for displaying said single projection.

23. A method for imaging a radiation portal of a high energy radiation therapy machine comprising the steps of:

(a) positioning a detector comprising a parallel array of ion chambers on a side of an object being treated opposite a radiation source;

(b) further positioning said detector at an initial measurement position;

(c) measuring an ionization current generated by each of said ion chambers for a predetermined time period, said ionization current being representative of the radiation absorbed by an ionizing medium in each of said ion chambers at said initial measurement position;

(d) converting each of said measured ionization current into digital data;

(e) individually filtering said converted data from each ion chamber of said detector;

(f) back-projecting said data from all of said ion chambers of said detector;

(g) moving said detector to a subsequent predetermined position by rotation about an axis formed by said radiation source and said object;

(h) measuring an ionization current generated in each ion chamber in said array of ion chambers at said subsequent position for said predetermined time period;

(i) further moving said detector through a predetermined series of orientations by rotation about said axis formed by said radiation source and said object;

(j) measuring ionization currents generated by each of said ion chambers at each of said orientations for said predetermined time period;

(k) converting each of said measured ionization current into digital data;

(l) individually filtering said converted data from each ion chamber of said detector;

(m) back-projecting said data from all of said positions of said detector; and (n) displaying said back-projection data on a video monitor.

24. A method defined in claim 23 wherein said step of individual filtering of said converted data is performed using a convolution filtering process.

25. A method as defined in claim 23 wherein the movement of the detector comprises rotation to discrete orientations about an axis formed by said radiation source and said object.

26. A method for imaging high energy radiation emanated from a radiation source and transmitted through an object comprising:

(a) positioning a detector comprising a plurality of parallel ion chambers on a side of said object opposite said radiation source in a predetermined initial position;

(b) measuring an amount of radiation transmitted from said radiation source through said object to said detector for a predetermined time period;

(c) rotating said detector through a predetermined sequence of orientations about an axis formed by said radiation source and said object;

(d) measuring an amount of radiation transmitted from said radiation source to each of said plurality of ion chambers of said detector at each orientation for said predetermined time period;

(e) converting each of said measurements to digital data;

(f) reconstructing an image of an irradiated area from said data and (g) displaying the image thus obtained.

27. A method as defined in claim 26 wherein said rotation of said detector is substantially continuous.

28. A method as defined in claim 26 wherein said rotation of said detector is performed incrementally, and further comprising the step of:

(h) holding said detector at each of said orientations for said predetermined time period.

29. A method as defined in claim 26 wherein said image reconstruction comprises the steps of:

(j) convolution filtering said digital data converted from each of said measurements;

(k) back projecting said digital data representative of all of said individual measurements after said convolution filtering has been performed; and (l) displaying said back-projection on a video monitor.

* * * * *
* * * * *

UNITED STATES PATENT AND TRADEMARK OFFICE
CERTIFICATE OF CORRECTION

PATENT NO. : 5,025,376

DATED : June 18, 1991

INVENTOR(S) : Frank J. BOVA ET AL

It is certified that error appears in the above-identified patent and that said Letters Patent is hereby corrected as shown below:

Column 12;
    Claim 7, line 35 :    delete "adsorbed" and insert -- absorbed --

Column 13;
    Claim 8, line 5 :    delete "adsorbed" and insert -- absorbed --

Claim 8, line 15:    delete "comprises" and insert -- comprise --

Claim 8, line 33:    delete "adsorb" and insert --absorb--

Column 14;
    Claim 12, line 1:    delete "adsorbed" and insert -- absorbed --

Column 15;
    Claim 23, lines 63-64: delete "current" and insert -- currents --

Column 16;
    Claim 23, lines 15-16: delete "current" and insert -- currents --

Signed and Sealed this

Thirteenth Day of October, 1992

Attest:

DOUGLAS B. COMER

*Attesting Officer*    *Acting Commissioner of Patents and Trademarks*